United States Patent [19]

Lavker et al.

[11] Patent Number: 5,556,783
[45] Date of Patent: Sep. 17, 1996

[54] METHODS OF CULTURING AND MODULATING THE GROWTH OF HAIR FOLLICULAR STEM CELLS

[75] Inventors: Robert M. Lavker, Malvern, Pa.; Tung-Tien Sun, Scarsdale; Jing-Shan Yang, New York, both of N.Y.

[73] Assignees: Trustees of Univ. of Penna, Philadelphia, Pa.; New York Univ., New York, N.Y.

[21] Appl. No.: 86,199

[22] Filed: Jul. 1, 1993

Related U.S. Application Data

[63] Continuation of Ser. No. 971,687, Nov. 4, 1992, Pat. No. 5,279,969, which is a continuation of Ser. No. 676,185, Mar. 27, 1991, abandoned.

[51] Int. Cl.$^6$ .............................. C12N 5/00; C12N 5/02
[52] U.S. Cl. .......................... 435/240.21; 435/240.2; 435/24.23; 435/240.243; 435/240.25
[58] Field of Search ..................... 435/240.2, 240.21, 435/240.23, 240.243, 240.25

[56] References Cited

U.S. PATENT DOCUMENTS

| | | | |
|---|---|---|---|
| 4,254,226 | 3/1981 | Eusinger et al. | 435/240.2 |
| 5,130,142 | 7/1992 | Wong et al. | 424/574 |
| 5,229,271 | 7/1993 | Philpott | 435/29 |
| 5,279,969 | 1/1994 | Lavker et al. | 436/63 |

OTHER PUBLICATIONS

Frater, Expercentia, vol. 32, pp. 675–676 (1976).
Weterings et al, British J. of Dermalology, vol. 104 pp. 1–5 (1981).
Jones et al, The Society of Invest Derm, vol. 1 pp. 58–64 (1988).
Schaart et al, *Hair and Hair Disease*, Chapt 13, pp. 301–324 (1989).
Roberts et al, J. Cell Physiol., 132(2) pp. 203–214 (1987).
Parkinson, Seminars in Cell Biology, vol. 3, pp. 435–444 (1992).
Philoptt et al, J. of Cell Sci, vol. 97, pp. 463–471 (1990).
Kurata et al, *Abstracts, World Congress of Dermatology*, Jun. 12–18, 1992, p. 127A.
Reynolds, J. of Invest Derm., vol. 101, No. 4, pp. 634–638 (1993).
Detmar et al, J. Invest Dermatol (US), 101 (Supp 1) pp. 1305–1345 (Jul. 1993).
Cotsarelis et al., An Improved Method for Detection of Epithelial Stem Cells, *J. Invest. Dermatol.* 92(3)(1989a).
Cotsarelis et al., Existence of Slow–Cycling Limbal Epithelial Basal Cells that can be Preferentially Stimulated to Proliferate: Implications on Epithelial Stem Cells, *Cell* 57:201–209 (1989b).
Cotsarelis et al., Label–Retaining Cells Reside in the Bulge Area of Pilosecbaceous Unit: Implications for Follicular Stem Cells, Hair Cycle, and Skin Carcinogenesis, *Cell* 61:1329–1337 (1990).

*Primary Examiner*—Marian C. Knode
*Assistant Examiner*—Susan M. Dadio
*Attorney, Agent, or Firm*—Law Offices of Jane Massey Licata

[57] ABSTRACT

A method of culturing hair follicular stem cells by isolating a subpopulation of follicular keratinocytes from the upper portion of a hair follicle, dispersing the isolated keratinocytes into a single cell suspension, and growing the dispersed isolated keratinocytes in the presence of 3T3 feeder cells is provided. A method of evaluating the efficacy of agents for modulating the activity of bulge cell populations by exposing bulge cells to an agent to be tested and comparing the response of the test cells to established controls for bulge cells is also provided. Methods of modulating the activity of hair follicular stem cells by identifying a subpopulation of follicular keratinocytes from the upper portion of a hair follicle and contracting the cells with a selected agent to stimulate growth or to selectively kill the cells is also provided.

7 Claims, 6 Drawing Sheets

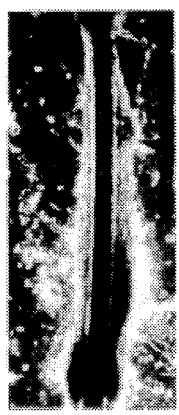  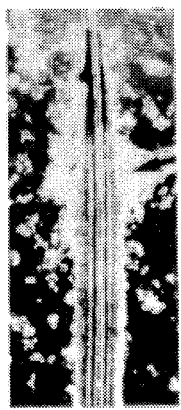   
FIG. 2a   FIG. 2b   FIG. 2c   FIG. 2d   FIG. 2e   FIG. 2f
  
FIG. 2g   FIG. 2h   FIG. 2i
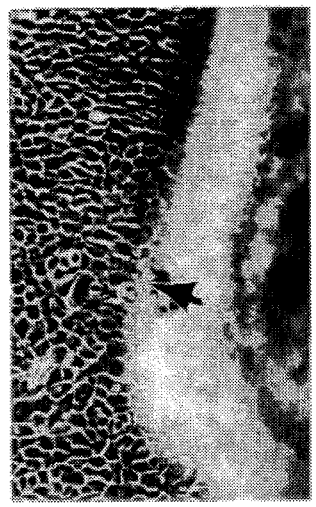 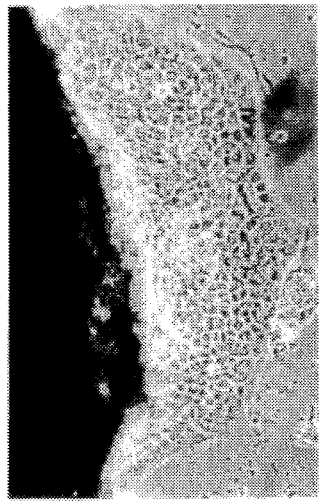 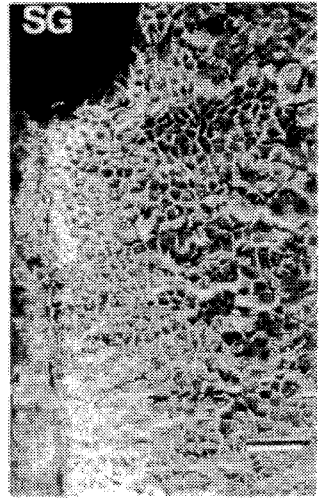
FIG. 2j   FIG. 2k   FIG. 2l

5,556,783

METHODS OF CULTURING AND MODULATING THE GROWTH OF HAIR FOLLICULAR STEM CELLS

INTRODUCTION

This application is a continuation-in-part of Ser. No. 07/971,687, filed Nov. 4, 1992, now U.S. Pat. No. 5,279,969, which is a continuation of Ser. No. 07/676,185, filed Mar. 27, 1991, now abandoned. The invention was made in the course of work supported by the National Institutes of Health. The Government may have certain rights in this invention.

BACKGROUND OF THE INVENTION

Stem cells are by definition present in all self-renewing tissues. These cells are believed to be long-lived, have a great potential for cell division and are ultimately responsible for the homeostasis of steady-state tissues. Stem cells rarely incorporate radioisotopes after single pulse labeling indicating that they are normally slow cycling. They can, however, be induced to enter the proliferative pool in response to certain growth stimuli. When stem cells undergo occasional cell division, they give rise to more rapidly proliferating "transient amplifying cells" ("TA") which incorporate a radiolabel such as tritiated thymidine ($^3$H-TdR) after a single exposure.

Stem cells possess many of the following properties: they are relatively undifferentiated, ultrastructurally and biochemically; they have a large proliferative potential and are responsible for the long term maintenance and regeneration of tissue; they are normally "slow-cycling", presumably to conserve their proliferative potential and to minimize DNA errors that could occur during replication; they can be stimulated to proliferate in response to wounding and to certain growth stimuli; they are often located in close proximity to a population of rapidly proliferating cells corresponding to the transient amplifying cells ("TA") in the scheme of (1) stem cell to (2) TA cell to (3) terminally differentiated cell; and they are usually found in well protected, highly vascularized and innervated areas.

Positive identification of stem cells has been difficult because there are no known immunological or biochemical markers specific for epithelial stem cells. Since they are normally "slow cycling", they cannot be labeled by single pulse administration of radioactive materials typically used to detect actively proliferating TA cells. It has been found that labeling of stem cells requires continuous labeling for a prolonged period. Once labeled, these slow-cycling cells retain isotope for an extended period of time. Such cells have been termed "label-retaining cells" or "LRCs".

Cotsarelis et al., *J. Invest. Dermatol.* 92(3)(1989a) disclose a method to facilitate detection of LRCs based on the ability of slow-cycling cells to be recruited to proliferate in response to hyperplastic stimuli. Alzet™ osmotic minipumps were intraperitoneally implanted in adult SENCAR mice to deliver 20 μCi of tritiated thymidine ($^3$H-TdR) per day for 14 days. During this labeling period, 0.01% O-tetradecanoylphorbol 13-acetate (TPA) in petroleum (Pet) was applied topically once daily for 4 days to the right flank. The contralateral side was treated with Pet only. Animals were sacrificed during and after labeling. TPA and Pet treated skin was examined by light microscopy and tissue section autoradiography. It was found that TPA treatment caused marked epidermal and follicular hyperplasia, whereas Pet treated sites did not appear morphologically altered. Fourteen days of continuous $^3$H-TdR resulted in greater than 90% labeling of all nucleated epidermal and follicular epithelial cells in both TPA and Pet treated sites. After 4 weeks, only a small number of cells remained labeled (LRCs). These cells were detected with greater frequency in TPA-versus Pet-treated epidermis. The most striking concentration of LRCs was found to occur in the follicular epidermis.

Using tritiated thymidine ($^3$H-TdR) labeling, a subpopulation of corneal epithelial basal cells located in the peripheral cornea in a region called the limbus, were identified by Cotsarelis et al., [Cell 57:201–209 (1989b)]. These cells are normally slow-cycling but can be stimulated to proliferate in response to wounding and to administration of TPA. The corneal epithelium appears to represent an exceptional situation. LRCs were detected in the basal layer of limbal epithelium. No such cells were detected in central corneal epithelium. It was found that limbal epithelium can be selectively stimulated to proliferate by introducing a wound 1–2 mm away in the central corneal epithelium. Preferential stimulation of limbal epithelial proliferation was also observed when TPA was topically applied to the anterior surface of the eye. It was therefore concluded that the limbal epithelium has a greater proliferative potential than central corneal epithelium.

Label-retaining cells were identified in mouse epidermis by continuously labeling with $^3$H-TdR using subcutaneous injections for seven days. This method labeled almost all epidermal cells. After chasing for four weeks, it was found that a subpopulation of epidermal basal cells maintained labeled-LRCs.

In other experiments, Alzet™ osmotic minipumps were implanted intraperitoneally in mice to deliver $^3$H-TdR for 14 days. Radioactive nucleic of over 95% of corneal epithelial cells and over 80% of limbal epithelial cells was observed. After a four week resting period, all of the radiolabeled cells disappeared from the cornea and few if any could be identified in limbal epithelium, suggesting that LRCs of the corneal-limbal epithelia must have an average cycling time much longer than 14 days and are therefore refractory to labeling under these experimental conditions.

To improve the chances of labeling these stem cells, they were recruited into a proliferative phase by wounding and application of TPA. These experiments showed the existence of a subpopulation of limbal basal cells that are normally slow-cycling but can be induced to proliferate and become labeled after appropriate stimulation.

Stem cells of various epithelia share a common set of features which are summarized in FIG. 7 of Cotsarelis et al. (1989b). The specific location and biological properties of corneal epithelial cells as well as the stem cells of a number of other epithelia including palmar (palm). epithelium, trunk epidermis, hair follicle, dorsal tongue epithelium, and intestinal epithelium are discussed. In FIG. 7(e) it is shown that in hair follicles, the heavily pigmented stem cells are located at the base, in close proximity with follicular papillae and associated vasculature. However, in subsequent work, Cotsarelis et al. [Cell 61:1329–1337 (1990)] show that the hair follicle stem cells were incorrectly identified. In fact, label-retaining cells were found to exist exclusively in the mid-portion of the follicle at the arrector pili muscle attachment site termed the "bulge" area of the hair follicle.

SUMMARY OF THE INVENTION

All self-renewing tissues by definition must contain stem cells that are relatively undifferentiated, and are normally slow-cycling but have a high proliferative potential. These stem cells play a central role in the long term maintenance of the tissue and in the pathogenesis of neoplasms and other diseases. Such cells can also serve as an important target for gene therapy. It has been shown that stem cells can proliferate in vitro better than their progeny cells. In the present invention, this approach was applied to the identification and isolation of hair follicular stem cells. Different subpopulations of follicular keratinocytes were isolated by microdissection, dispersed into a single cell suspension, and grown in the presence of 3T3 feeder cells. The keratinocytes were subcultured under comparable conditions in order to compare their in vitro life span. The results indicate that the life span of keratinocytes of the upper follicle (containing mainly the isthmus area) is>sebaceous gland and>lower follicle (between the bulge and the bulb),>bulb (containing the matrix cells). The cultured upper follicle cells tend to be small and relatively uniform in size. These results show the existence of follicular stem cells in the upper follicle.

Cells cultured in accordance with the methods of the invention can be used to evaluate the efficacy of agents for modulating the activity of such cells. Such methods would be useful for identifying agents which stimulate hair growth or to prevent hair loss, for example. Cultured cells may also be used for follicular reconstruction and transplantation as well as for wound coverage in burn or skin-ulcer patients.

DESCRIPTION OF THE DRAWINGS

FIGS. 2a–2b are a series of photographs showing outgrowth of upper follicular epithelial cells. Intact, microdissected human hair follicles were placed in plastic dishes in DF medium-containing 17% fetal calf serum and other additives for 5–12 days. Note the formation of epithelial outgrowth in the upper follicle (UF), most frequently in a region below the sebaceous gland (SG). This area shows a change in the follicular diameter which is obvious in normal histological sections but becomes even more prominent after the follicles have been placed in culture for several days. Histological examination showed that this area corresponds to the bulge. FIGS. 2(a) to 2(f) show 6 different follicles with such epithelial outgrowth (arrows), and FIGS. 2(g) to 2(l) show under a higher magnification the phase contrast morphology of such cells. Scale bar in FIGS. 2(f) and 2(l) equal to 400 um and 100 um, respectively.

FIGS. 3(a) and 3(b) show the results from two independent experiments. Note that, comparing with other keratinocytes, cells from the upper follicles have a longer in vitro life span and form larger colonies.

DETAILED DESCRIPTION OF THE INVENTION

Figure 1:
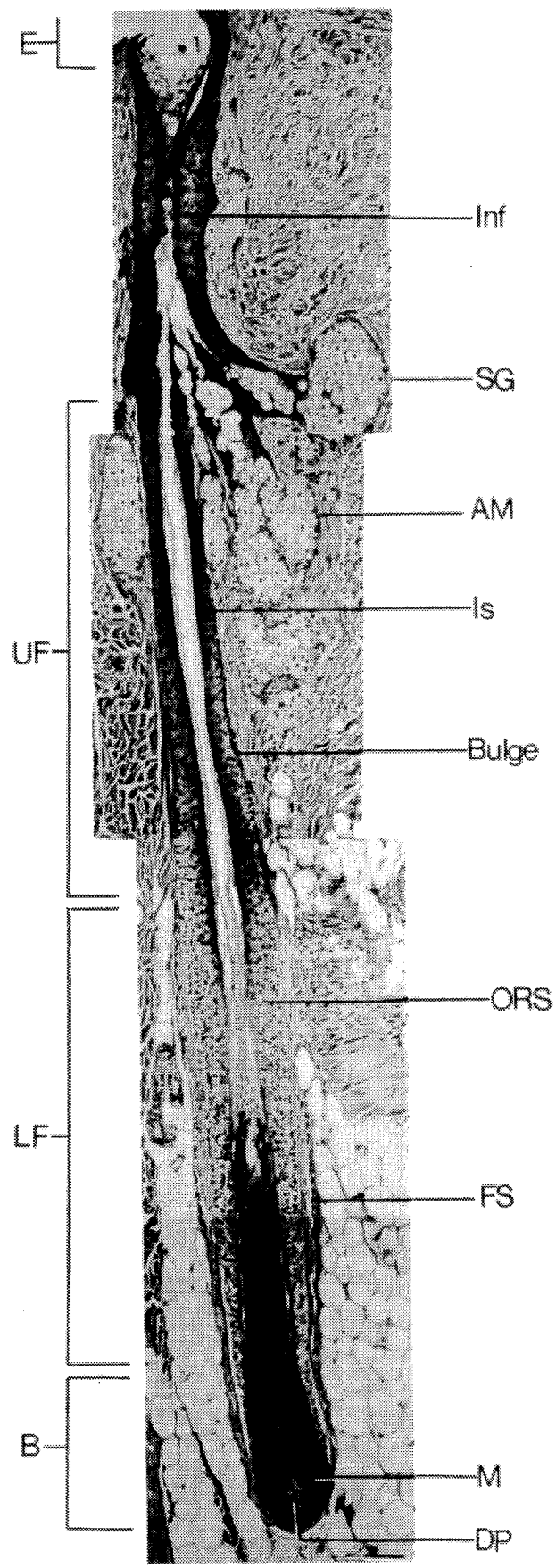
FIG. 1 is a photograph showing different parts of a human anagen hair follicle. Follicles were microdissected, and later separated into the "upper follicle" (UF), "lower follicle" (LF), "bulb area" (B) as defined on the left. Abbreviations are: E (epidermis), Inf (infundibulum), SG (sebaceous gland), AM (arrector pili muscle.), Is (isthmus), ORS (outer root sheath), FS (fibrous sheath), M (matrix) and DP (dermal papillae. Hematoxylin eosin-stained plastic section. Bar= 200 um.

The inventors have located, identified, and isolated the putative stem cells of the hair follicle, sebaceous gland and epidermis. Using autoradiographic techniques designed to detect slow-cycling cells (label-retaining cells; LRCs), it was surprisingly found that there were very few LRCs in the epidermis. Furthermore, when the hair follicle was surveyed, the inventors determined that there were no LRCs in the matrix cells comprising the bulb, which is the region taught by the prior art to contain follicle stem cells. Rather, the inventors determined that there was a subpopulation of LRCs in the upper portion of the follicle in a region known as the "bulge".

The bulge is a subpopulation of outer root sheath cells located in the mid-portion of the upper follicle at the arrector pili muscle attachment site. The prior art taught that hair follicle stem cells reside in the matrix or lower bulb area of the hair bulb. The inventors' discovery provided insight into hair cycle control and the involvement of hair follicle stem cells in skin carcinogenesis and led to the development of methods for identifying and modulating the activity of these bulge cells for diagnostic and therapeutic purposes and for evaluating the efficacy of agents for modulating the activity of such cell populations.

One of the most distinguishing features of stem cells is their slow cycling nature. A single pulse of a radioisotope such as $^3$H-TdR will not label stem cells; labeling requires repeated administration of the isotope for a prolonged period of time. Once labeled, cells that cycle slowly retain isotope for an extended period of time.

A discrete population of mouse hair follicle cells was identified. These cells are slow cycling but can be induced into the proliferative phase in response to hyperproliferative stimuli. The location of these cells was unexpected. The stem cells were not found in the matrix area of the bulb where follicular stem cells were thought to reside. Rather, the cells were identified in a specific area of the outer root sheath, the bulge. The bulge structure is not unique to the hair follicle of the mouse. Outer root sheath bulges are also found in human hair follicles, as well as trunk and neck skin. The bulge area had attracted so little attention by prior art workers that it is rarely even mentioned in histology text books. The realization that the hair follicle stem cells reside in the bulge area has provided new insights to the inventors into how the hair cycle is regulated and the involvement of hair follicles in skin carcinogenesis.

THE BULGE ACTIVATION THEORY

The hair cycle involves three distinct phases: anagen (growing), catagen (regressing), and teleogen (resting). The inventors have developed a new understanding of how the hair cycle is controlled. The bulge stem cells are activated by dermal papilla during late telogen. This is termed "bulge activation". The dermal papilla are activated by the matrix during mid-anagen. Matrix cells are in fact TA cells; therefore, contrary to the teachings of the prior art, matrix cells have a limited proliferative potential. The upward movement of dermal papilla is important for the activation of hair stem ells. Defects in any of these elements could result in abnormal hair growth of hair loss.

In addition, it has been found that stem cells of the hair follicle are also involved in and are largely responsible for experimental tumor formation in mouse skin.

THE HAIR FOLLICLE

Hair follicle is an epidermal appendage, the lower part of which undergoes cycles of growth and degeneration. During the anagen (the growing phase) of the hair cycle, matrix keratinocytes located in the bulb region grow vigorously generating cells that differentiate into several distinct hair components including the medulla, cortex and inner root sheath. During catagen, keratinocytes of the lower follicle below the bulge region (the attachment site of the arrector pili muscle) degenerate and the dermal papilla cells (DP; a group of specialized mesenchymal cells) aggregate and becomes encapsulated by a connective tissue sheath. Through the contraction of this sheath, the DP aggregate ascends and becomes attached to the bottom of the upper (permanent) portion of the follicle (telogen or the resting phase). Finally, a new epithelial growth originates from the bottom of the bulge area; this downgrowth pushes the DP away and reforms a growing bulb.

A centrally important feature of a stem cell is its high proliferative potential, which usually outlasts the life span of the animal. Although it is hard to assess the in vivo potential of different subpopulations of follicular cells, their in vitro potential can be compared. The usefulness of cell culture as a way to identify stem cells is demonstrated in the present invention.

The in vitro growth potential of different subpopulations of follicular epithelial cells were compared. Keratinocytes of different portions of human scalp follicles were isolated by microdissection followed by trypsinization and propagated in the presence of 3T3 feeder cells. The results indicate that the upper follicle (a region including the bulge) contains keratinocytes that have in vitro proliferative potential that is significantly higher than those of the lower follicle, the bulb, the sebaceous gland and, unexpectedly, the epidermis.

Human hair follicles were microdissected from plastic surgery skin specimens. In one series of experiments, microdissected, intact human hair follicles were placed in explant cultures. The advantage of this approach is that the sebaceous gland and the characteristic change in the diameter of the follicle around the bulge area provide markers for determining rather precisely the origin of the outgrowth. Results indicate that the most frequent site of such outgrowth is located below the sebaceous gland in an area coinciding with a change in follicular diameter. Histological examinations established that this area corresponds to the bulge. FIGS. 2a–f show 5 such follicles, and FIGS. 2g–l show, under a higher magnification, the morphology of cells outgrowing from the bulge areas of these follicles.

Figure 3A:
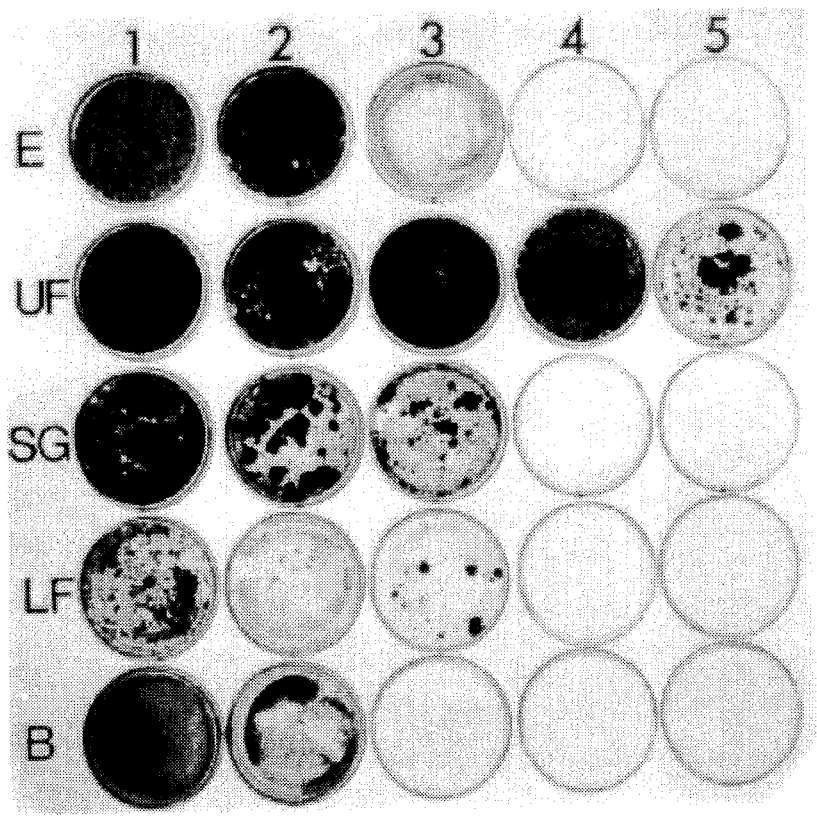
FIG. 3a–3b are a photograph showing the results of serial cultivation of different subpopulations of human skin keratinocytes. Hair follicles were microdissected into several parts (see FIG. 1) including the epidermis (E), upper follicle (UF), sebaceous gland (SG), lower follicle (LF) and bulb (B). The keratinocytes ere dispersed by trypsin/EDTA, plated in the presence of 3T3 feeder cells, and subcultured at approximately 70% confluency. The numbers on top 1, 2 denote secondary, tertiary cultures, respectively. Only secondary and subsequent subcultures are shown because primary cultures showed large variations in colony density and thus were not strictly comparable.
Figure 3B:
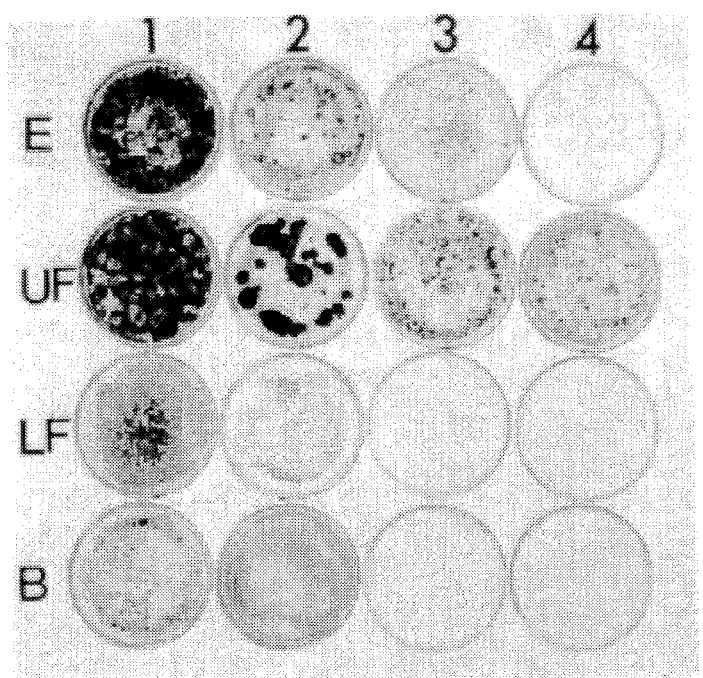
Figure 4A:
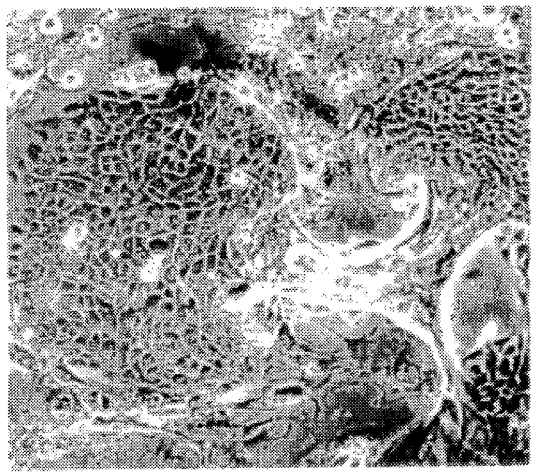
FIG. 4l–4e are a series of photographs showing cultured keratinocytes of interfollicular epidermis (FIGS. 4a and 4b), lower follicle (FIGS. 4c and 4d), and bulb (FIG. 4e). All these cells were 10 days (secondary) cultures grown in the presence of a 3T3 feeder layer. Scale bar=10 um.
Figure 4B:
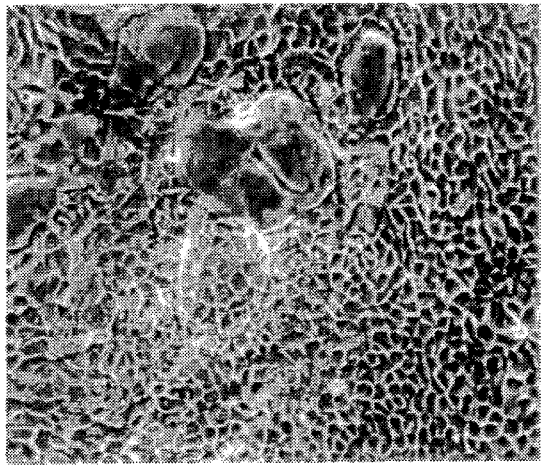
Figure 4C:
Figure 4D:
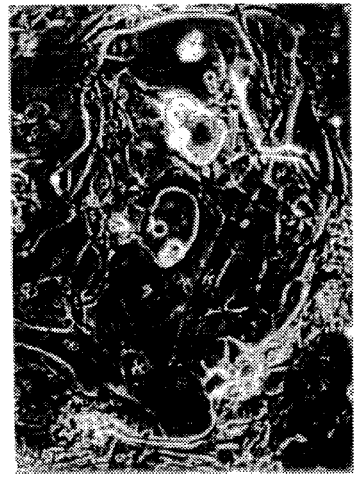
Figure 4E:
Figure 5A:
FIG. 5a–5e are a series of photographs showing cultured human sebocytes. Sebaceous glands (SG) were microdissected (FIG. 5a), and placed in petri dish to obtain sebocyte outgrowths (FIGS. 5b and 5c), which were then trypsinized and plated in the presence of 3T3 feeder cells. Oil red O-staining (FIG. 5e) of a 10 day culture showed that many sebocytes accumulate lipids (arrows), while some other cells were negative (open arrows). The scale bars in FIG. 5(d) and 5(e) equal to 100 um and 50 um, respectively.
Figure 5B:
Figure 5C:
Figure 5D:
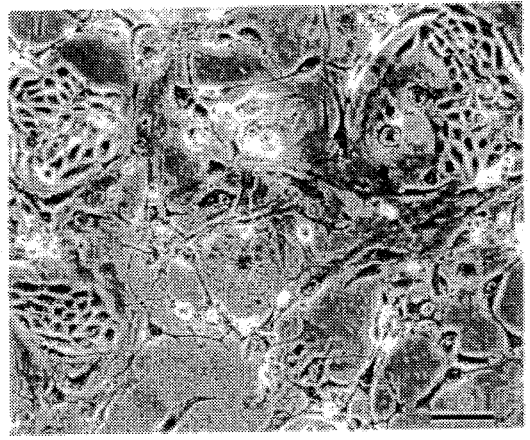
Figure 5E:
Figure 6A:
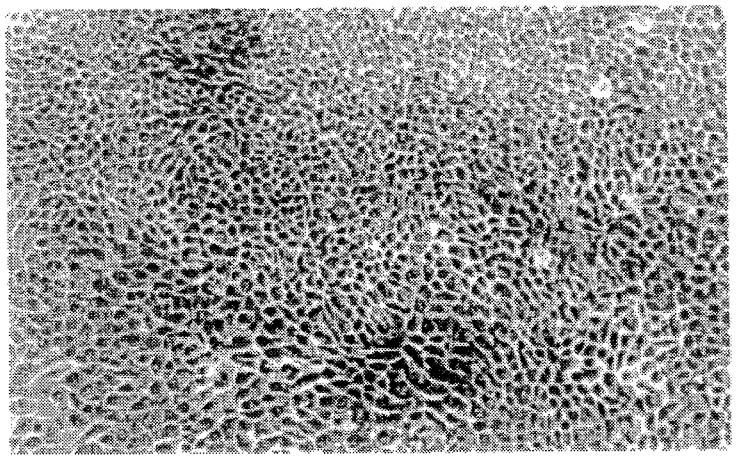
FIGS. 6a–6d are a series of photographs showing keratinocytes cultured from upper human hair follicles. These are primary cultures that have grown for 7–10 days in the presence of 3T3 feeder cells. Cells of many colonies are relatively small and uniform in size (FIGS. 5a and 5b, compared with FIGS. 6c and 6d). Scale bar=10 um.
Figure 6B:
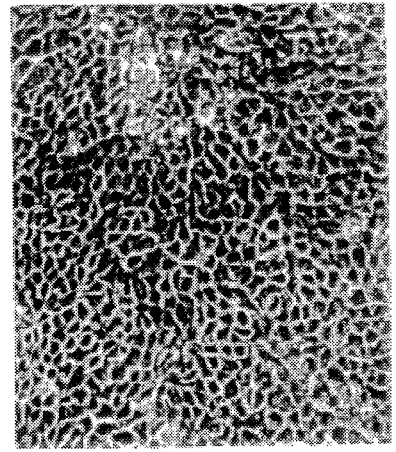
Figure 6C:
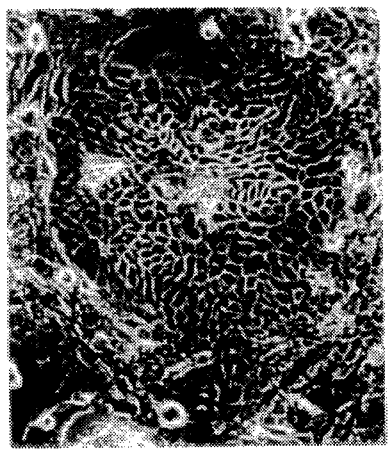
Figure 6D:
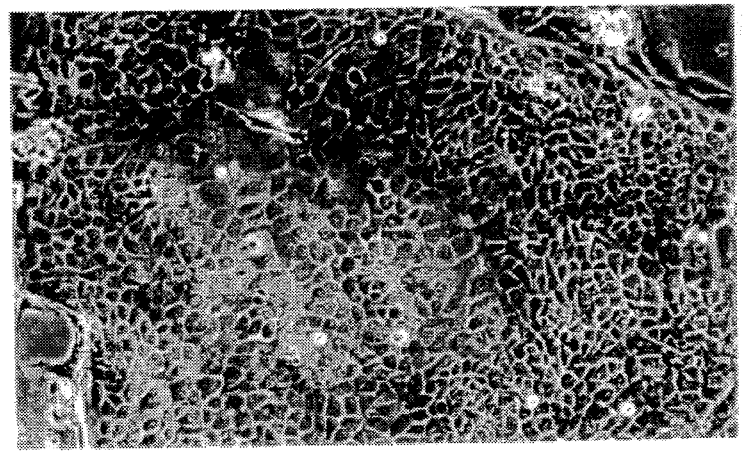

One problem in interpreting the explant culture data is that one cannot rule out the possibility that keratinocytes of the lower follicles or the bulb area were hindered from forming outgrowth by the intact connective tissue sheath. To test this possibility, the epidermis, upper follicle, sebaceous gland, lower follicle, and bulb, (as shown in FIG. 1) were dissected and dissociated into single cell suspensions using EDTA and trypsin, and plated them in the presence of mitomycin-treated 3T3 feeder cells. These cells were allowed to grow to about 70% confluence and then passaged under identical conditions. FIGS. 3a and 3b show the results of two typical experiments. In these experiments, the epidermal cells grew quite well, and could be subcultured 2–3 times, Keratinocytes of the lower follicles grew well initially in the primary culture, but upon subculturing quickly undergo senescence forming predominately small colonies with signs of terminal differentiation (FIG. 4c and d). The growth of bulb cells, even in primary culture, was relatively poor; they form small colonies containing highly refractile, upper cells reminiscent of the keratinized structures formed by epidermal cells in vitamin A deficient media (FIG. 4e). Cells of the sebaceous gland grew as well as the epidermal keratinocytes, forming colonies that were morphologically similar to keratinocytes although some of the cells apparently accumulated lipids (FIG. 5).

Interestingly, cells of the upper follicles grew extremely well (FIG. 6). In five independent experiments, it was found that upper follicular cells could be passaged 2–3 more times than keratinocytes of the epidermis, sebocytes, and the bulb (FIG. 3). In all of these experiments, the bulb cells showed the poorest growth, most likely reflecting a special nutritional requirement. An interesting feature of these cultured upper follicular cells is that they frequently form colonies with "uniformly small cell" (FIG. 6), suggesting that these cells are relatively young with a high proliferative potential.

The data clearly show that the upper human follicle (including the bulge region) contains a subpopulation of keratinocytes that have a greater in vitro proliferative potential than the rest of the follicle including the lower follicle and sebaceous gland. These cells have been successfully cultured and identified. The proliferative potential of the cells can be assessed and used to determine the effect of selected agents on their growth. For example, these cells can be cultured, exposed to a selected agent and their proliferative potential determined and compared with untreated cultures. In this way agents which stimulate hair growth, for example, could be easily identified.

Methods of evaluating the efficacy of agents for modulating the activity of bulge cell populations are provided. Methods of the invention comprise exposing the cells to an agent to be tested and comparing the response of the test cells to established controls for bulge cells. Cell number and/or viability relative to established controls may be determined. Such methods would be useful for evaluating agents to stimulate hair growth or prevent hair loss, for example. Further, such methods would be useful for identifying agents useful for the treatment of skin cancers.

Methods of modulating the activity of such cells, for example, stimulating them to promote tissue growth or selectively killing them for permanent hair removal, are also provided. Methods of the invention comprise identifying the cell populations in selected tissue and inducing the cells into a proliferative phase. Such methods would be useful for stimulating hair growth or preventing hair loss, for example. Such agents may be administered either internally or topically, either alone or in combination with a pharmaceutically acceptable carrier.

In conclusion, it has been shown that upper human anagen follicles contain a subpopulation of keratinocytes that can grow better than all other skin keratinocytes including those of the lower follicle, sebaceous gland and, surprisingly, even the epidermis. The data also indicate that follicular stem cells may be involved not only in initiating the formation of a new, lower follicle during early anagen, but also in the long-term maintenance of sebaceous gland the epidermis. Cultured upper follicular keratinocytes may therefore be useful for follicular reconstruction and transplantation, as well as for wound coverage in burn or skin-ulcer patients. Results also suggest that the selective killing of upper follicular keratinocytes in situ could constitute an effective step for permanent hair removal.

The invention is further illustrated by the following, non-limiting examples.

EXAMPLES

Example 1 The Identification of Slow Cycling Cells in Hair Follicles

Twice daily subcutaneous injections of 3 H-TdR were given to newborn mice over the first seven days of life resulting in labeling of almost 100% of nuclei in mouse epidermis, hair follicles, sebaceous glands fibroblasts and endothelial cells. Following a four week resting period ("chase"), no LRCs were identified in the matrix area of the hair follicles indicating that matrix does not contain slow-cycling cells. Unexpectedly, groups of LRCs were found in midfollicle, in the bulge region.

In another set of experiments, adult mice were implanted with Alzet™ osmotic minipumps continuously delivering $^3$H-TdR for two weeks. After a four week chase period, LRCs were found exclusively in the bulge region.

Upon application of TPA, normally slow-cycling cells within adult bulges were stimulated to proliferate. Once the external stimulation was removed, the bulge cells were apparently the only ones that returned to their previously slow-cycling state, retaining their label for a long period of time.

Example 2 Localization of Cytokine Receptors

Previous studies of cytokine/proliferative relationships were done on purified populations of isolated cells. The following experiments using organ culture and relevant in vivo models are designed to asses cytokine effects on epithelial proliferation within the context of an intact microenvironment.

In studies designed to determine the localization of receptors for cytokines, bitinylated cytokines are added to explants of murine skin in the range of 0.5–50 mg/ml. Tissues are incubated with cytokines for 60 minutes, rinsed thoroughly, and then incubated in medium alone for 10 minutes. Immunohistochemical localization of the cytokine is accomplished using a sensitive avidin biotin immunoperoxidase or immunoalkaline phosphatase stain in accordance with standard techniques.

Example 3 Effect of Cytokines of Slow Cycling Cells

In studies designed to determine the effects of cytokines on various proliferative cell populations, selected cytokines are added to explants of murine skin. Explant cultures are serially harvested at daily intervals for the first 4 days of exposure, and cytokine effects on $^3$H-TdR incorporation assessed in accordance with standard techniques.

In another set of experiments, a cohort of mice is continuously labeled for 2 weeks with $^3$H-TdR and then allowed to rest for 4 weeks. Once labeled, cells which cycle slowly retain the isotope for an extended period of time and are thus identified as label retaining cells. Cytokines are introduced via intradermal injection to continuously labeled/chased animals. Four hours prior to sacrifice, colcemide (4 mg/kg) is injected intraperitoneally. Animals are sacrificed at 2, 6, 12 and 24 hours after cytokine injection and skin from injected areas fixed and processed for autoradiography according to routine procedures. Appearance of labeled mitotic figures indicates that slow cycling cells have been induced to proliferate.

Example 4 Isolation and Organ-Culture of Human Hair Follicles

The surface of human skin from the nape of the neck, obtained from plastic surgery was shaved, wiped with 70% ethanol, and the tissue was then incubated in Dulbecco's modified Eagles' Medium (DMEM) containing penicillin (100 unit/ml), streptomycin (100 mg/ml) and amphotericin B (0.5 mg/ml) for 30 minutes. Most of the subcutaneous fat was dissected away taking care not to damage the hair follicles, and the skin was trimmed to small pieces (4×8 mm$^2$). These skin fragments were incubated at 4° C. for 12 hours in Dispase II (0.2 mg/ml; Boehringer, Mannheim, Germany) in phosphate-buffered saline (PBS). Hair follicles were dissected and placed in separate dishes containing DF medium (a 3:1 mixture of DMEM and Ham's F12 media supplemented with 17% fetal calf serum, 0.5 mg/ml of hydrocortisone, 10 mg/ml EGF, $10^{-9}$M colera toxin, 3.4 mM L-glutamine, 5 ug/mL insulin, and 0.135 mM adenine.

Example 5 Culture of Subpopulations of Follicular Cells

Each isolated follicle was cut into several segments as shown in FIG. 1. Briefly, the "upper follicle" represents the upper two fifths of the follicle excluding the infundibulum and sebaceous gland. The "lower follicle" contains the lower half to three fifths of the follicle excluding the bulb. The "upper follicle", "lower follicle" and "bulbs" were dissociated into single cells by incubating at 37° C. for 30 minutes in 0.125% trypsin and 0.01% EDTA in PBS. The dissociated cells were rinsed in PBS containing 5% calf serum and incubated in 0.25% deoxyribonuclease for 5 minutes. The resulting cell suspensions were filtered through three layers of sterile gauze and 200 μm mesh nylon, collected by centrifugation, and plated in DF complete medium in the presence of mitomycin C-treated 3T3 feeder cells. The keratinocytes were subcultured by trypsinization followed by plating them at $10^5$ cells/35 mm dish in the presence of mitomycin C-treated 3T3 feeder cells.

We claim:

1. A method of culturing hair follicular stem cells comprising:

isolating from the upper portion of a hair follicle a subpopulation of follicular keratinocytes comprising hair follicular stem cells;

dispersing said isolated keratinocytes into a single cell suspension; and growing said dispersed isolated keratinocytes together with 3T3 feeder cells or in a serum-free medium, thereby producing a hair follicular stem cell culture.

2. The method of claim 1 wherein said subpopulation of follicular keratinocytes is isolated by microdissection.

3. The method of claim 1, wherein said subpopulation of follicular keratinocytes comprises outer root sheath cells located in the midportion of the upper follicle at the arrector pili attachment site.

4. The method of claim 1 wherein said 3T3 feeder cells are mitomycin-treated.

5. The method of claim 4 wherein the cells are allowed to grow to about 70% confluence.

6. The method of claim 1 wherein the isolated keratinocytes are dispersed by incubating at about 37° C. for about 30 minutes in about 0.25% trypsin.

7. The hair follicular stem cell culture produced by the method of claim 1.

* * * * *

UNITED STATES PATENT AND TRADEMARK OFFICE
CERTIFICATE OF CORRECTION

PATENT NO. : 5,556,783

DATED : September 17, 1996

INVENTOR(S) : Lavker et al.

It is certified that error appears in the above-indentified patent and that said Letters Patent is hereby corrected as shown below:

Column 4, line 5, please delete "41" and insert therefor --4a--

Column 4, line 24, plese delete "5a and 5b" and insert therefor --6a and 6b--

Signed and Sealed this

First Day of July, 1997

Attest:

BRUCE LEHMAN

Attesting Officer    Commissioner of Patents and Trademarks